United States Patent
Saadat et al.

[11] Patent Number: 5,954,714
[45] Date of Patent: Sep. 21, 1999

[54] HEATED BALLOON HAVING ROTARY FLUID IMPELLER

[75] Inventors: Vahid Saadat, Redwood Shores; John J. McIntyre, San Carlos; Gail Stevens, Menlo Park, all of Calif.

[73] Assignee: Gynecare, Inc., Menlo Park, Calif.

[21] Appl. No.: 08/752,501

[22] Filed: Nov. 20, 1996

[51] Int. Cl.⁶ ................................................. A61B 17/38
[52] U.S. Cl. .............................. 606/28; 606/41; 607/104
[58] Field of Search ................................ 606/27, 28, 41; 607/104, 105; 366/244

[56] References Cited

U.S. PATENT DOCUMENTS

| | | | |
|---|---|---|---|
| 4,953,985 | 9/1990 | Miller | 366/244 |
| 5,084,044 | 1/1992 | Quint | 606/27 |
| 5,443,470 | 8/1995 | Stern et al. | 607/98 |
| 5,460,628 | 10/1995 | Neuwirth et al. | 606/28 |
| 5,571,153 | 11/1996 | Wallsten | 607/98 |
| 5,653,692 | 8/1997 | Masterson et al. | 604/113 |

*Primary Examiner*—Jennifer Bahr
*Assistant Examiner*—Roy D. Gibson
*Attorney, Agent, or Firm*—Emil Richard Skula

[57] ABSTRACT

Apparatus for thermal coagulation having an improved circulation assembly and heating assembly. The apparatus includes a balloon catheter secured to and in fluid communication with a handle for inserting the apparatus into a human uterus. A distensible bladder is secured to the distal end of the catheter and encloses a heating assembly having a tubular core configured with a spiral groove which retains a heating filament. An impeller having at least two blades is positioned distal of the heating assembly and includes a cable having a distal end secured to the impeller. The impeller cable is partially disposed in the handle, in the elongate tubular member and in the core of the heating element, such that axial rotation of said cable rotates the blades of said impeller. During use of the apparatus, the distensible bladder is inflated with a fluid to a desired pressure and rotation of the impeller blades is initiated. The inflation fluid within the distensible bladder is heated to a desired temperature, which is maintained for a desired time interval. The inflation fluid within the distensible bladder is allowed to cool and rotation of the impeller blades is terminated. Thereafter, the inflation fluid is removed from the balloon catheter to deflate the distensible bladder.

21 Claims, 8 Drawing Sheets

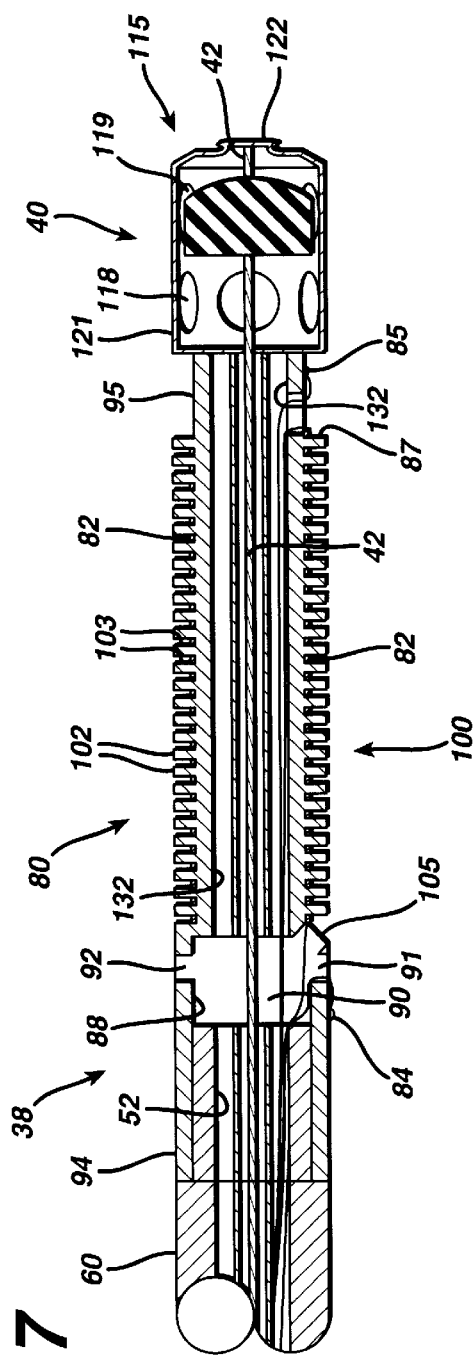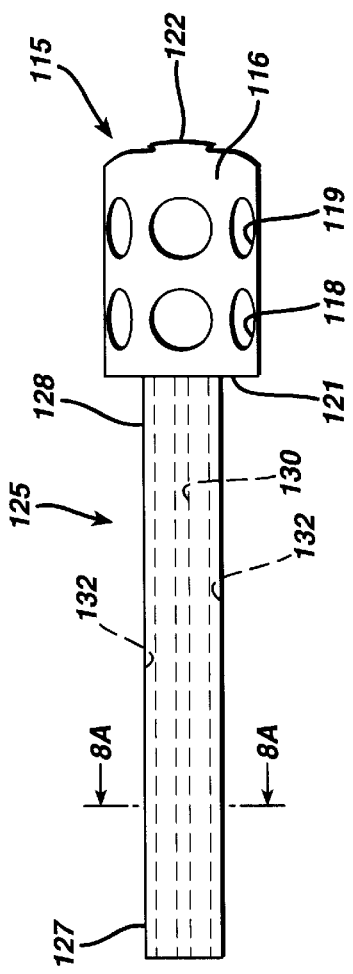

HEATED BALLOON HAVING ROTARY FLUID IMPELLER

BACKGROUND OF THE INVENTION

The present invention relates generally to an apparatus for thermal coagulation and more particularly to a system for applying heat to the endometrium of a human uterus of the type comprising a heated balloon catheter having a rotary impeller for improved circulation of fluid within a distensible bladder.

The following terms as used herein have the meaning given below:

"Menorrhagia" means a condition of excessive menstrual bleeding in women.

"Thermal coagulation" means the application of heat to tissue in an amount sufficient to destroy the tissue.

"Necrosis" means the death of cells in tissue.

"Endometrium" is that portion of the inner lining of the uterus to which an embryo normally attaches and is responsible for the menstrual cycles.

Apparatus and methods utilizing heated balloons or similar distensible bladders have been used to treat menorrhagia in women. Patients and physicians may prefer treatment of menorrhagia with a heated balloon, because such a minimally invasive procedure effectively curtails the excessive uterine bleeding associated with menorrhagia without requiring surgical removal of the uterus. Such balloon therapy involves inserting and inflating a balloon with a fluid into the uterus. After balloon inflation, the fluid is heated to a temperature for a period of time that coagulates, ablates, necroses, or destroys the endometrium (mucous membrane) and perhaps a portion of the myometrium (muscular layer). A successful endometrial ablation procedure requires controlling the temperature of the balloon. If the heating of the endometrial lining continues longer than necessary for thermal coagulation of the endometrium, then the myometrium could be irreparably damaged.

Temperature fluctuations and gradients along the surface of the balloon adversely affects an operator's control over endometrial thermal coagulation. Temperature fluctuations and gradients are, in part, caused by convection currents of the fluid within the balloon and the presence of an insulating, static boundary layer of fluid along the inner wall of the balloon. While cooler fluid moves toward the bottom of the balloon, the warmer, less dense fluid rises. When the fluid within the balloon is subject to such convection during heating, considerable temperature fluctuations along the surface of the balloon may result, causing less than optimal results. Mechanical circulation or agitation of fluid within the balloon has been known to improve the temperature consistency over the surface of the balloon.

Some balloon catheters circulate fluid by means of separate inlet and outlet passages that connect the balloon with an external heating element. Heat is circulated from the external heating element through the inlet passage into the balloon. Then, the fluid from the balloon is returned to the external heating element through the outlet passage. Such a catheter design requires the hot fluid to pass through the vagina and the opening of the cervix, which may cause physical discomfort or possible tissue damage as heat is conducted through the catheter walls. Since the hot fluid must travel a significant distance between the external heating element and the balloon surface being heated, control over temperature of the balloon surface is difficult.

Other known heated balloon catheters circulate fluid via a pair of one way valves mounted within a housing located at the end of a fluid delivery tube. The housing is surrounded by an inflatable member, such as a balloon. The first valve permits fluid flow from the housing into the balloon. The second valve permits flow from the balloon into the housing. The valves respond to alternating pressure differentials between the balloon and the housing created by an external bellows or piston which causes pulses of fluid to move up and down the fluid delivery tube. Such a configuration requires circulating hot fluid from the balloon into the fluid delivery tube, creating a risk of causing discomfort to the patient or vaginal tissue damage.

Another balloon catheter design known in the art places a propeller or pump wheel within a lumen of a tubular housing contained within the balloon. Such a configuration creates axial fluid motion or motion substantially parallel to the axis of rotation. However, because the propeller is contained within the housing, any axial fluid flow results in mostly linear flow through the tubular housing and a generally linear current within the balloon. Thus, the heating of the balloon surface may not be uniform and the fluid may not properly circulate around the cornua of the uterus where the endometrium is usually the thickest. Another problem with this approach is the lack of sufficient cross section of the lumen to prevent a sufficiently low resistance to passing the fluid through the housing and into the balloon. Thus, vigorous circulation may not be possible so as to prevent a boundary layer of fluid from forming along the inner surface of the balloon.

Other balloon catheter configurations which have limited effectiveness or practicality are known. One such design places a longitudinally vibrating member at the end of a heating element within a balloon. Another design places a flat shape memory alloy at the end of the heating element, such that the shape memory alloy responds to electrical impulses to move the alloy in a lateral fanning motion, thereby somewhat circulating the fluid within the balloon. Each of these designs may work with varying degrees of effectiveness, but have yet to provide a practical configuration and cost effective solution for providing uniform heating of the balloon surface. Thus, heretofore, there was a need for a circulation system that causes vigorous agitation of fluid within the distensible bladders of a balloon catheter in a safe and effective manner.

SUMMARY OF THE INVENTION

Briefly and in general terms, the present invention provides an apparatus and method for thermal coagulation having an impeller for vigorous circulation and an improved heating assembly. The improved system includes heating of an inflation medium within a distensible bladder secured to a balloon catheter and positioned adjacent the endometrium and within the uterus of a patient. The apparatus introduces the inflation medium under pressure into the distensible bladder so as to assure substantially uniform contact of the bladder with the endometrium. The present invention includes an improved heated balloon catheter having a rotary impeller to create radial fluid motion around a heating assembly disposed within the balloon or distensible bladder. The radial flow impeller creates a vortex within the balloon causing efficient mixing of the fluid surrounding the heating element. The impeller moves the fluid so as to effectively limit temperature gradients and fluid boundary layers along the balloon surface. In addition, the fluid path includes otherwise secluded portions of the balloon, such as those proximate a cornu of the uterus.

The system also provides for controlling the temperature and pressure of the inflation fluid for a desired period of time while the distensible bladder is within the uterus. The improved heating assembly includes a heater filament disposed within a spiral groove formed in a core member to prevent the balloon from contacting the filament, thereby eliminating the need for a protective shell around the core of the heating assembly. The heating element core is disposed within balloon and is configured with one or more thermocouples. This improved heating assembly provides a highly responsive and effective mechanism for maintaining an even temperature profile throughout the surface of the balloon.

The apparatus of the present invention comprises a balloon or distensible bladder configured on the distal end of a catheter tubular member. Within the catheter is a fluid delivery lumen for filling and draining the balloon. Mounted at the distal end of the catheter tubular member and within the balloon is a heating assembly which increases the temperature of the fluid in the inflated balloon. Extending longitudinally through the lumen in the catheter and through the heating element is a rotary drive shaft, axle or cable. One or more flexible blades are secured to the distal end of the rotary drive axle. As the drive axle is rotated, the blades also rotate, causing fluid motion within the fluid filled balloon.

The flexible blades are generally flat and rectangular in shape, extending radially from the cable. However, for the purpose of having a small profile during insertion of the catheter into the uterus, the blades may be spiral wrapped around the cable to create a compact configuration. The resistance from the fluid unfurls the blades when the cable rotates the blades.

The impeller blades are made of thin strips of latex, silicone, polyurethane, polyethylene rubber, polyethylene (PE) or polyethylenetherapthalate (PET) or other suitable polymeric and flexible material having elastomeric properties. The use of a flexible material for the impeller blades has the advantage of not causing trauma or damage to the balloon walls if the rotating impeller contacts the sides of the balloon. Contact between the blades and the balloon walls could occur as a result of abnormal shape of the patient's uterus.

An atraumatic cap or protective cage may be disposed proximate the distal extremity of the heating element core to protect the balloon from trauma that could result from contact with the rotary drive cable or impeller blades. Such an impeller cage retains the impeller blades away from the sides of the balloon. The drive cable is slidably and rotatably mounted within a lumen of the tubular member of the balloon catheter and through the heating element core mounted on the distal end of the tubular member.

The proximal end of the balloon catheter assembly is secured to a handle body configured to be held in and operated by a human hand. The proximal end of the handle is configured with a fluid fill port connected to and in fluid communication with an inflation lumen of the balloon catheter. A valve is disposed between and in fluid communication with the inflation lumen and a fluid fill port. A syringe may be connected to the fluid fill port to inflate the distensible bladder with inflation medium to a desired pressure.

An umbilical cable is partially disposed within the handle body and terminates with an electrical connector secured to the heating element filament and thermocouples. In addition, the umbilical cable is configured with a rotary connector secured to the impeller drive cable and with a pressure port in fluid communication with the inflation lumen of the balloon catheter. The umbilical cable connectors are removably secured to a system controller which regulates the temperature while monitoring the pressure of the fluid in the balloon catheter. Also, the controller initiates and terminates the rotation of the impeller drive cable so as to safely and effectively control the thermal coagulation process.

In summary, the system of present invention includes an apparatus for thermal coagulation. The apparatus comprises an elongate tubular member having a first lumen in fluid communication with its proximal end and its distal end. The apparatus further comprises a handle secured to the proximal end of the elongate tubular member and in fluid communication therewith. A distensible bladder or balloon is secured proximate the distal end of the elongate tubular member and is in fluid communication with its first lumen. A heating assembly (element) having a tubular core is secured to the distal end of the tubular member and is disposed within the balloon. The core may be configured with a spiral groove which retains a heating filament. A rotary impeller having at least two blades is positioned distal of the heating assembly and is secured to the distal end of a rotation cable. The impeller cable is partially disposed in the handle, in the elongate tubular member and in the core of the heating assembly, such that axial rotation of said cable rotates the blades of said impeller.

In further summary, the system of present invention includes a method which provides an apparatus for thermal coagulation as disclosed herein. A distensible bladder is inflated with a fluid to a desired pressure. The method further includes initiating axial rotation to a cable so as to rotate the blades of an impeller. The inflation fluid within the distensible bladder is heated to a desired temperature, which may be accomplished by providing electric current to a resistive wire of the heating element. The temperature within the distensible bladder is maintained for a desired time interval and then the inflation fluid within the distensible bladder is allowed to cool to a desired temperature. The axial rotation of the cable is terminated so as to stop the blades of the impeller from rotating. Thereafter, the inflation fluid is removed from the balloon catheter to deflate the distensible bladder.

These and other features and advantages of the invention will become apparent from the following more detailed description, when taken in conjunction with the accompanying drawings which illustrate, by way of example, the principles of the invention.

BRIEF DESCRIPTION OF THE DRAWINGS

FIG. 7 is a partial side cross-sectional of the heating assembly of the present invention.

FIG. 8 is a side plan view of the impeller cage assembly of the present invention.

FIG. 8A is an end-sectional view of the impeller cage insert of FIG. 8 taken along the lines 8A—8A.

DETAILED DESCRIPTION OF THE INVENTION

Figure 1:
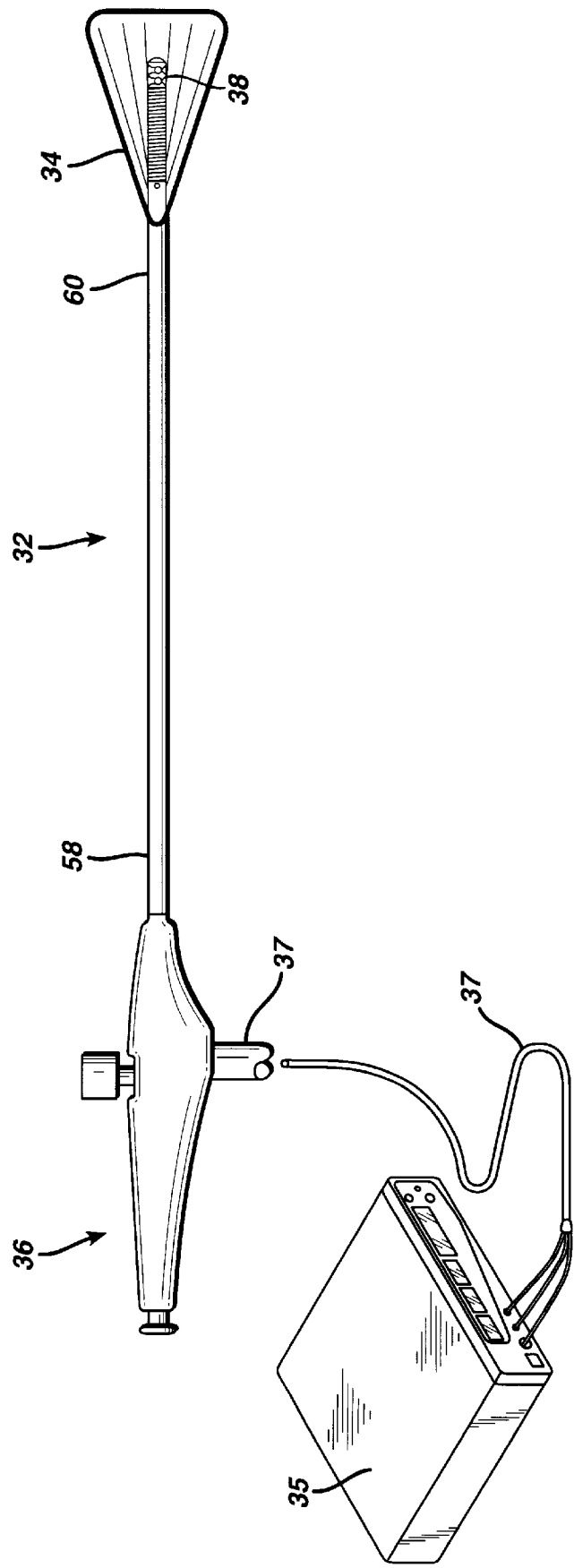
FIG. 1 is perspective view of the balloon catheter apparatus, controller and cable drive mechanism of the present invention.

As shown in the drawings for purposes of illustration, the present invention is embodied in a heated balloon catheter apparatus having a rotary impeller and drive cable for circulating inflation and heating fluid within a distensible bladder. The inventive apparatus and method utilize a heated distensible bladder to treat menorrhagia in women by inserting a balloon catheter into the patient's uterus and inflating the balloon with the fluid, such as saline or aqueous sugar solution. After balloon inflation, the fluid is heated to a temperature for a period of time that coagulates, ablates, necroses, or destroys the endometrium and perhaps damages the myometrium. Such treatment of menorrhagia is desirable, because the procedure effectively curtails the excessive uterine bleeding associated with menorrhagia without requiring surgical removal of the uterus.

A successful endometrial ablation procedure requires controlling the temperature of the surface of the balloon and the fluid within. Temperature fluctuations and gradients along the surface of the balloon adversely affects physician control over endometrial necrosis. Temperature fluctuations and gradients are, in part, caused by convection currents of the fluid within the balloon and formation of a static, insulating boundary layer of fluid along the inner surface of the balloon. Vigorous mechanical circulation or agitation of fluid within the balloon improves the temperature consistency along the surface of the balloon.

In accordance with the present invention, and as shown in FIG. 1, a heated balloon catheter apparatus 30 having circulation means includes a catheter or tubular member 32 having a distal end disposed within a distensible bladder or balloon 34. A handle assembly 36 is secured to the proximal end of the catheter tubular member and is configured for manipulation by the physician or other user. A controller 35 may be connected to the handle by an umbilical cable 37. Alternatively, the balloon catheter may be connected to a simple power source for heating fluid within the distensible bladder.

Figure 2:
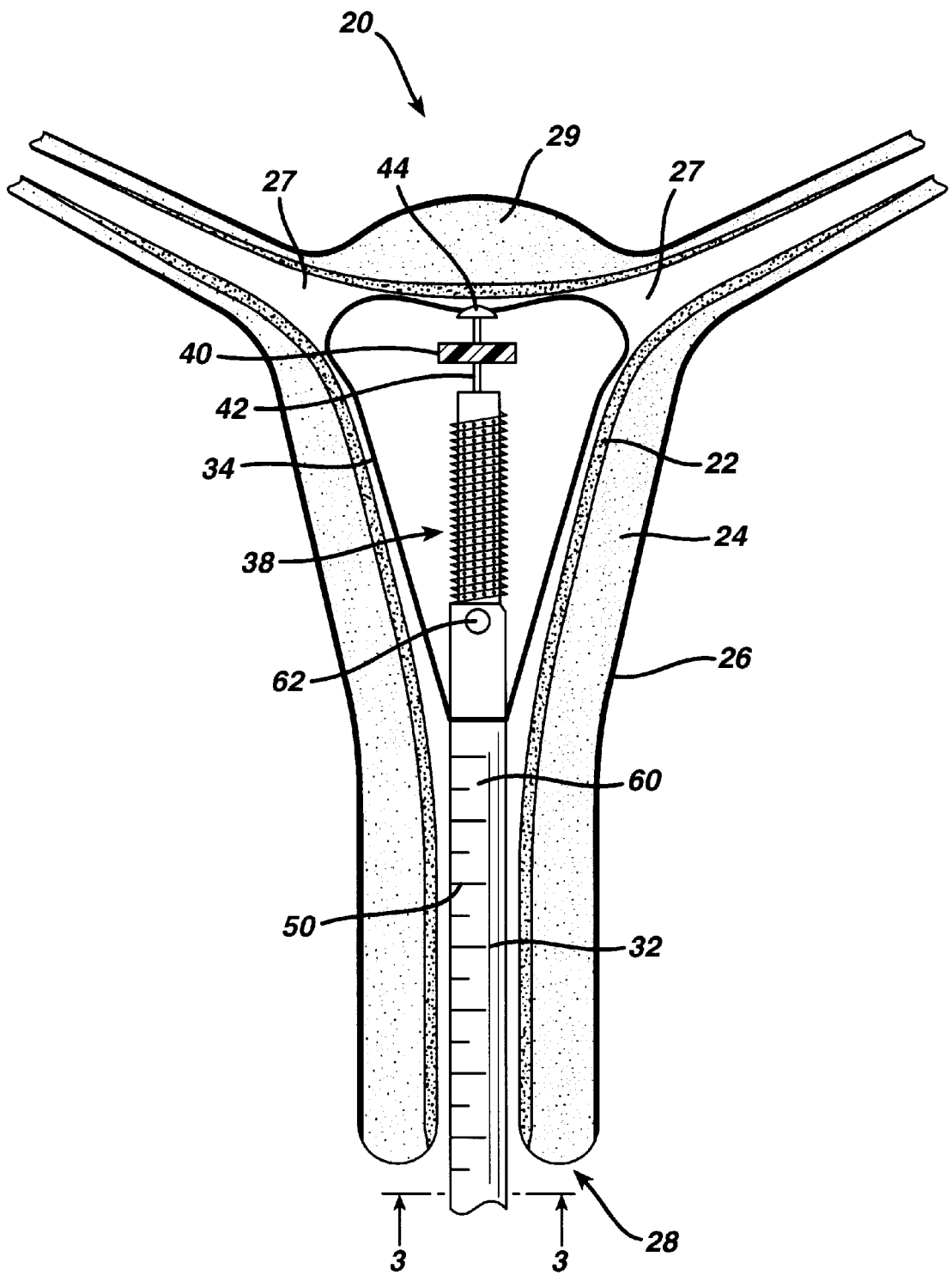
FIG. 2 is a partial cross-sectional of a heated balloon catheter apparatus of the present invention disposed within a human uterus.

With reference to FIG. 2, the distal end of the balloon catheter tubular member 32 is configured to be inserted within the uterus 20 of a human patient without traumatizing or damaging patient tissue. The uterus is comprised of three basic layers, i.e., the endometrium 22, the myometrium 24 and the outer layer or serosa 26. The balloon catheter is inserted into the uterus through the cervix 28 and proximate the fundus 29. A heating assembly 38 is disposed within the balloon 34 and is secured to the distal end of the catheter tubular member. The balloon is configured to conform to the shape of the uterus so as to provide heat transfer from the heating assembly to the endometrium. The distal portions of the balloon substantially extend into each cornu 27 of the uterus.

Also enclosed with the balloon 34 is a rotary impeller 40 driven by a rotary drive cable or axle 42 which is partially disposed within the tubular member and heating element 38. The impeller causes the fluid to move in a rotary fluid path around the balloon. The rotary fluid path is similar to a vortex or whirlpool which eliminates temperature differentials along the surface of the balloon, including the portions of the balloon proximate the cornua 27.

Referring to FIG. 2, the balloon catheter shaft or tubular member 32 is formed from an elongated tubing made of semi-rigid material, for example, acrylonitrile-butadiene-styrene (ABS), polyvinyl-chloride (PVC) or polyurethane to permit easier insertion into the uterus, while providing support needed to manipulate the balloon 34. The tubular member has sufficient length from balloon to the catheter handle 36 to extend through a patient's vagina, through the cervix 28 and into the uterus 20. Placement of the apparatus may be aided by virtue of scale gradations 50 configured directly on the tubular member to indicate the depth of insertion of the balloon.

Figure 3:
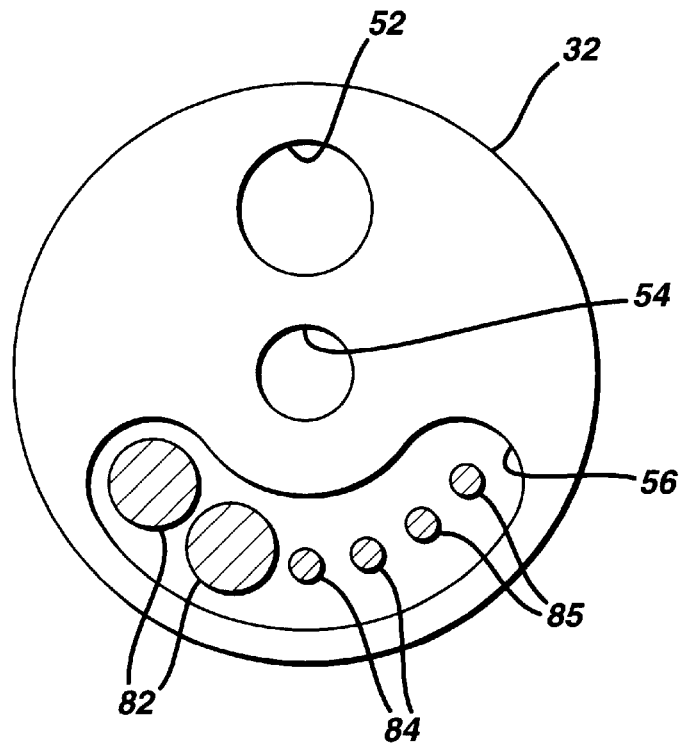
FIG. 3 is an end-sectional view of the catheter of FIG. 2 taken along the lines 3—3.

As shown in more detail in FIG. 3, the catheter tubular member 32 has at least one fluid passage or lumen 52, a cable lumen 54 and a wire lumen 56. The fluid passage and lumens of the catheter may be annular, hemispherical or otherwise suitably shaped for the particular function of the lumen. Each lumen extends from the handle 36 at the proximal end 58 of the tubular member to the distal end 60 of the tubular member. The lumens may be arranged radially, concentric or any other suitable configuration which retains the structural integrity of the catheter shaft.

Each of the three catheter lumens serve a specific function. Saline or similar liquid for inflating and heating the balloon 34 passes through the fluid lumen 52. A fluid port is configured in the handle 36 at the proximal end of the tubular member 32 to allow the operator to fill or drain fluid from the balloon. The distal end of the fluid lumen is connected to a fluid vent 62 in the heating element core which provides fluid communication with the fluid passage and the balloon.

The impeller drive cable 42 preferably extends through the center lumen 54 of the catheter shaft 32. The cable is positioned centrally within the lumen so that contact along the length of the drive cable with the wall of the catheter is minimized so as to reduce friction. The proximal end of the cable lumen is coupled to the umbilical cable 37, which is secured to the handle 36 for connecting the cable to a drive mechanism located in the system controller 35. The distal end of the lumen is coupled to a lumen in the heating assembly 38.

The wire lumen 56 contains the electrical leads for the thermocouples and heating element wire. The leads extend from the proximal end 58 of the catheter tubular member to catheter distal end 60. The proximal end of the wire lumen is coupled to the handle 36 and umbilical cable 37 for electrical connection to the system controller 35 or other power source. The distal end of the lumen is coupled to an exit port which allows connection of the leads to the thermocouples and heating assembly filament. The catheter may be configured without a wire lumen by running the electrical leads through the fluid lumen 52 or the cable lumen 54.

The distensible bladder or balloon 34 preferably is made of latex, silicone or other elastomeric/material and has a general pear shape. It is approximately three to five centimeters long and when inflated is capable to fill the uterine cavity and exert a pressure against the endometrium 22. The shape of the uterine cavity is not round but is flattened proximate the fundus 29. Since the balloon in its inflated state conforms to the shape of the uterus, the inflated balloon will be flattened at its distal portion.

The balloon 34 must be capable of withstanding high temperatures without rupturing, and preferably have as good a heat transfer characteristic as is obtainable in such materials to provide efficient heat transfer to tissue. A distensible bladder of a sturdy, heat resistant material, such as latex rubber or silicone, has been found satisfactory. The inflation medium or heating fluid preferably should be a sterile nontoxic fluid. A five percent dextrose in water solution has been found satisfactory.

As shown in FIG. 2, the rotary drive cable 42 is retained within the catheter tubular member 32 and extends through the core of the heating assembly 38. The distal end of the cable is rotatably affixed at its distal end to an atraumatic cap 44. The atraumatic cap is affixed to the balloon 34 and protects the balloon from contact with the rotary impeller 40. The rotary impeller comprises a plurality of rotary blades that are fixed around the drive cable. The impeller blades may be made of latex strips, polyethylene (PE), polyethyletheraptalate (PET) or other suitable material.

The impeller drive cable 42 is 0.5 to 1.0 millimeters in diameter. It has some flexibility but is preferably made of stainless steel or spring steel. A co-axially wound cable is also suitable. The cable extends the entire length of the balloon catheter apparatus 30 from the distal end of the balloon 34 to the handle 36. In addition to being able to rotate, the drive cable can be slid longitudinally through the catheter and heating element.

Figure 4:
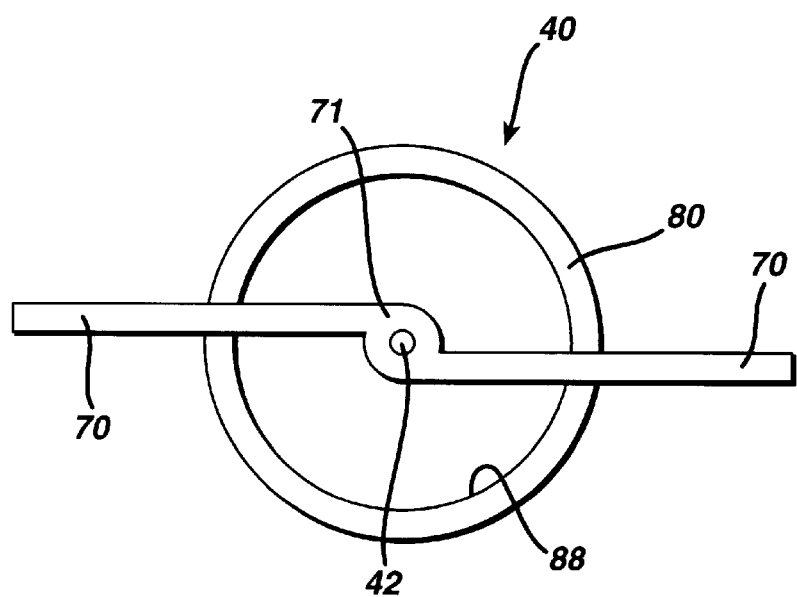
FIG. 4 is an end plan view of the catheter and impeller of FIG. 2, wherein the impeller blades are unfurled.
Figure 5:
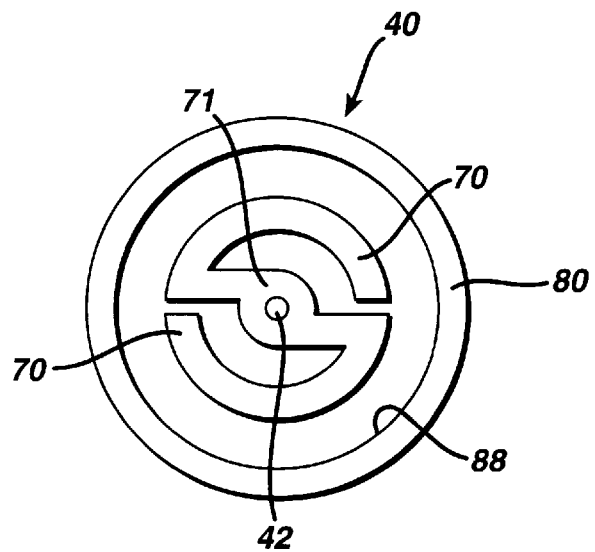
FIG. 5 is an end plan view of the catheter and impeller of FIG. 2, wherein the impeller blades are wrapped around the impeller cable.

As shown in FIGS. 4 and 5, the impeller 40 is comprised of at two blades 70 axially spaced apart around the drive cable 42. Alternatively, the impeller may be configured with four or more blades. The blades can be made of latex, silicone or similar elastomer and have a thickness of about 0.2 to 0.4 millimeters. Prior to deployment of the catheter into the uterus, the blades are wrapped in the same direction as the rotating cable. For example, if the impeller rotates in a clockwise direction, the blades should be wrapped around the cable in a clockwise direction.

Impeller drive cable 42 extends from the lumen 88 in the core 80 of the heating assembly 38. The blades 70 extend axially or radially from the central base 71. The impeller is affixed to the drive cable by extending the drive cable through the central base and fixing the blades to the base. Well known bonding methods may be used to ensure that the blades are securely fixed to the base and cable.

Referring again to FIG. 2, an atraumatic cap 44 is positioned distal to the impeller blades 70. The atraumatic cap is rotatably affixed to the rotary drive cable 42. The atraumatic cap is made of a plastic polymer with good heat transfer properties. The cap is rounded on its distal side and has a diameter comparable to the diameter of the heating assembly core 80. The proximal side of the cap may be sized and shaped to fit against the distal end of the core of the heating element.

The atraumatic cap 44 is axially aligned with the heating assembly 38 and is centrally affixed to the balloon 34. This feature ensures that the heating element and fluid impeller 40 is centered within the balloon to the extent that the patient's anatomy will allow. Centering the impeller assembly creates symmetrical turbulence within the balloon thereby reducing friction on the blades from the fluid and reducing asymmetric loading on the impeller. Such a centered configuration thus reduces power consumption to drive the impeller cable and blades. The atraumatic cap is bonded to the balloon by one of the various means known to those skilled in the art such as mechanical bonding, ultrasonic welding, adhesive bonding, crimping or any combination of the above that may prove to be effective. Alternatively, the heating assembly core, impeller distal end and impeller cage may be disposed within, but not connected to the distensible bladder.

Figure 6:
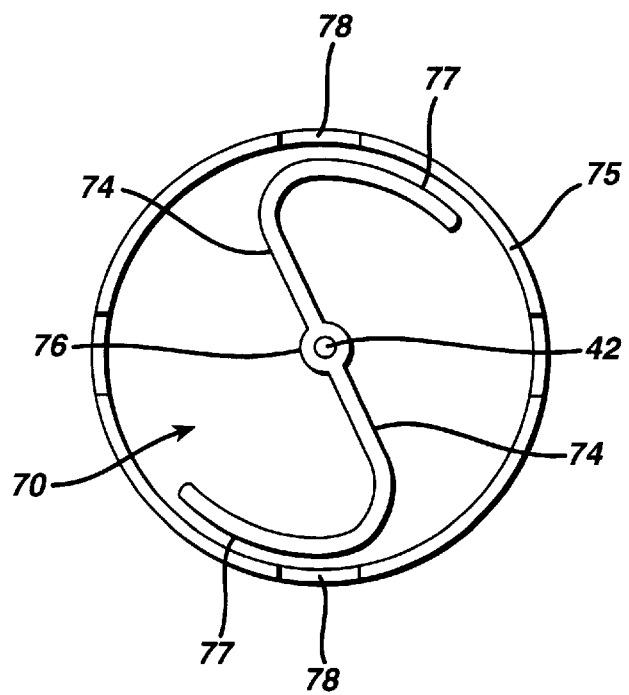
FIG. 6 is an end plan view of the catheter and impeller of FIG. 1, wherein the impeller blades are disposed adjacent and within the impeller cage.

As shown in FIG. 6 the impeller blades 74 may be configured to touch against a cap or cage 75 which surrounds the impeller assembly 40. The blades can be formed by injection molding or blow molding from a polymer, such as PE or PET. The impeller is configured with a plurality of, for example, two, equally spaced apart blades formed in a low profile and furled manner. Such a blade configuration includes a central base 76 with a bore configured to receive the impeller drive cable 42. Each blade has a thickness of approximately 0.3–0.6 millimeters and a width ranging from three to ten millimeters and a length comparable to the outer radius of the heating assembly core 80. The advantage of using PET or PE for the blades is that such polymers have considerable memory and will return to their original shape after rotation of the impeller ceases. The polymer is heat treated to have memory in a furled configuration.

Each polymer blade 74 is curved around the base 76 such that the ends 77 of the blades rest against the inside of the cage 75. The cage prevents the blades from contacting the balloon 34. Thus, the blades preferably have a span significantly greater than the diameter of the heating assembly core 80 and catheter tubular member 32. The cage has a diameter about the same as the catheter tubular member to maintain a low profile (cross-section) and is configured with a plurality of ports 78 which allow fluid flow from the cage into the balloon and from the balloon into the cage. The action of the rotating impeller blades causes vigorous circulation of fluid within the balloon and about the heating assembly. Such circulation is especially important, and provided by this configuration, proximate the fundus 29 where the endometrium 22 of uterus 20 is the thickest.

As depicted in FIG. 2, an atraumatic cap 44 is provided to prevent the rotary impeller 40 and impeller cable 42 from contacting the balloon 34. The impeller is positioned from the end of the balloon by the distance of three to five millimeters. The impeller blades 70 are sized so that the span of the rotating blades does not exceed the width of the distal end of the inflated balloon. Such a configuration ensures that the rotating blades will not contact or damage the wall of the balloon. Contact of the blades with the balloon will not necessarily traumatize the balloon, especially if the blades are formed from latex or similarly pliable material. Therefore, the span of the impeller blades may be configured considerably larger than the diameter of the heating assembly core 80 and atraumatic cap (FIG. 4).

It is important that the balloon catheter apparatus 30 have a profile (cross-sectional diameter) that is as narrow as possible when the apparatus is inserted into or removed from the uterus 20. A narrow profile makes positioning of the balloon 34 less traumatic to the cervical tissue. On the other hand, it is desirable after the balloon is positioned and inflated to have impeller blades 70 with as great a span as possible. The larger the span of the rotating apparatus blades, the more vigorous will be the fluid circulation.

The heating assembly core lumen 88 may be configured to receive the rotary impeller 40 prior to deployment and rotation of the impeller blades 70. In addition, the blades are retracted into the core lumen after the therapy procedure and just prior to balloon deflation and removal of the balloon catheter apparatus 30 from the uterus 20. Each of the blades is wrapped around the impeller drive cable 42 in the same direction that the drive cable is rotated, forming a generally rounded compact configuration, as illustrated in FIG. 5.

In the retracted state, the rotary impeller 40 fits snugly within the core lumen 88 proximate the heating assembly core distal end 95. When the impeller is retracted, the atraumatic cap 44 abuts against the distal extremity of the heating assembly core. The cap is designed to conform to the shape and size of the core. The blades are deployed for rotation by sliding the impeller cable in a distal direction until the atraumatic cap rests against the fundus 29 of the uterus 20. Once the balloon 34 has been inflated with fluid, the elastomeric blades 70 are in direct contact with the fluid in the balloon. The impeller cable 42 is rotated by an external rotary drive in the system controller 35 (FIG. 1) which causes the blades to unwind as they meet resistance from the fluid in the balloon. The centrifugal force of the blades maintains the blades in an extended state during rotation.

Figure 9:
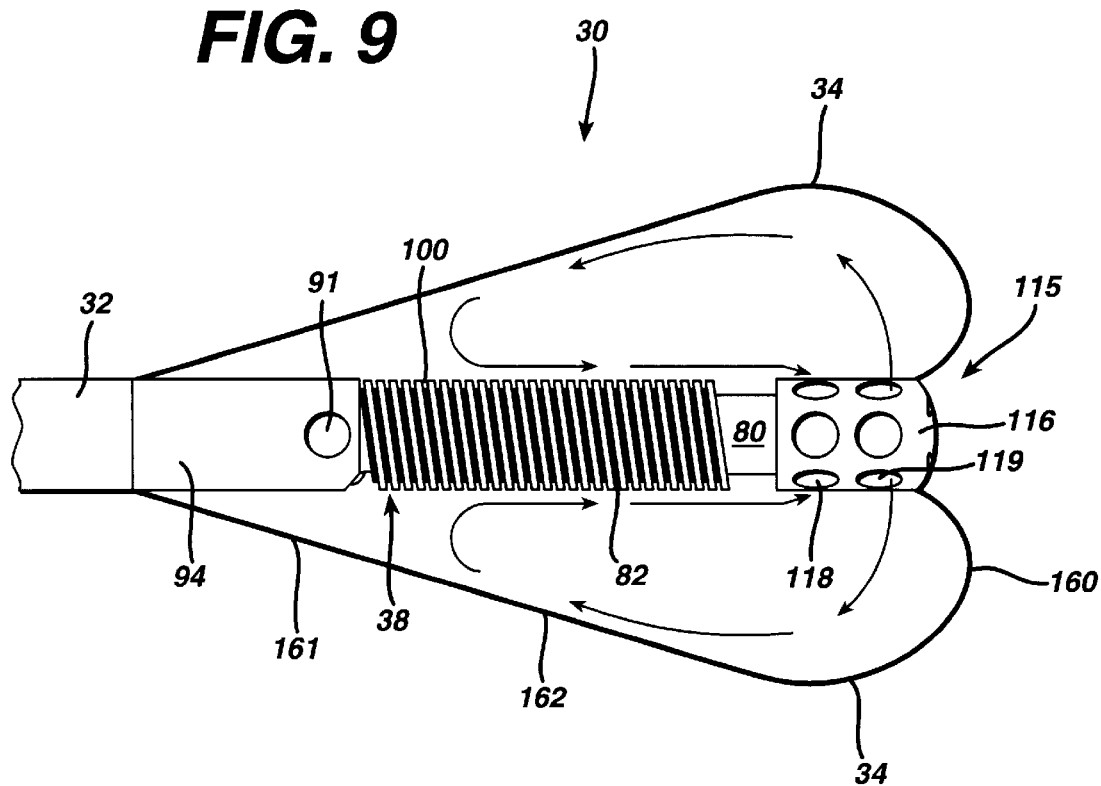
FIG. 9 is a side cross-sectional enlarged view of the distal portion of the balloon catheter assembly of the present invention.

Referring to FIG. 7, a heating element or assembly 38 is configured to fit over or otherwise connect to the distal end of the catheter tubular member 32 and extends partially through the balloon 34 (FIG. 9). The heating assembly comprises a core 80, a heater filament or wire 82 wrapped around the core and preferably a pair of thermocouples 84, 85. The heating assembly core is configured with a lumen 88 which slidably and rotatably retains the impeller drive cable 42. The center of the core lumen is aligned with and coupled to the catheter cable lumen 54. The heating element core and the catheter tubular member may be integrally formed from a single tube.

The heating assembly core 80 is further configured with a fluid lumen 90 having a plurality of vents 91, 92 positioned proximate the proximal end 94 of the core. The vents are in fluid communication with the fluid passage 52 of the catheter tubular member 32 and with the cavity formed within the balloon 34. The catheter fluid lumen is connected to a valve assembly and fluid fill port in the catheter handle assembly 36. Thus, fluid may be supplied from an external source, e.g., a syringe, to inflate and heat the balloon.

The thermocouples 84, 85 are positioned proximate the proximal end of the heating assembly core 80. The thermocouples are secured distal the fluid vents 91, 92 along the outer surface 87 of the core, preferably on opposite sides of the core. A single thermocouple or plurality of thermocouples may be used and positioned along the surface of the heating assembly core to provide adequate monitoring and control of the fluid temperature within the cavity formed within the balloon 34. Each thermocouple is connected to leads disposed in the wire lumen 56 of the catheter tubular member 32, which is coupled to an electrical connector in the catheter handle assembly 36.

The heating assembly core 80 is approximately four centimeters long and preferably has a diameter of about five to ten millimeters. The thickness of the core wall from the outside surface 87 to the cable lumen 88 is preferably from 0.05 to 1.0 millimeters. The heating assembly core is axially centered within the distensible bladder or balloon 34. The core proximal end 94 may be an integral part of the catheter tubular member 32 or may be fixably mounted over or otherwise secured to the distal end 60 of the catheter tubular member.

The outer surface of the heating assembly core 80 should be able to withstand the high temperatures reached by the fluid in the balloon 34. In addition, the core should be formed from material having good heat distributing properties. Thus, the core may be made of ABS plastic, such as that which the catheter tubular member is formed, or the core may be made of stainless steel or a suitable ceramic material.

The heating assembly core 80 is formed with a spiral groove 100 in its outer surface 87. The spiral groove is configured to receive the heater filament 82 as the wire is helically wrapped around the core. The groove forms crests 102 and troughs 103 along the core surface from just distal the fluid vents 91, 92 to just proximal the distal end 95 of the heating assembly core.

The helically wrapped heater filament 82 may be formed in a loop terminating at the distal end 95 of the core, or may be formed from a single strand of wire or bundled filament. The proximal ends of the heater filament pass through a port 105 proximate the fluid ports 91, 92 at the core proximal end 94. The heater filament ends are connected to the heater wire leads in the wire lumen 56 in the catheter tubular member 32. The proximal ends of the heater wire leads pass through the catheter handle 36 and are attached to an electrical connecter at the proximal end of the umbilical cable 37, which is removably connected to a temperature controller or power supply externally located from the balloon catheter apparatus 30 (FIG. 1). The heater filament is made from copper, nickel, nickel-chromium or similar resistive wire. Other heating filaments known to those skilled in the art may be used.

With reference to FIG. 7, spiral groove 100 has a depth in each trough 103 which is greater than the diameter of the heater filament or wire 82. The pitch of the groove is dependent upon the length of the heating wire used and upon the length of the heating assembly core 80. It is important that the groove depth be about twice the size of the groove width (distance between crests) to ensure the balloon does not contact the heater filament. Alternatively, the spiral groove troughs may have a width just smaller than twice the thickness of the balloon to prevent the balloon from entering the groove. If the balloon is permitted to touch the heater filament, then the balloon may melt and/or rupture, causing hot fluid to flow into the uterus. The spiral groove of the present invention prevents such a problem.

The heater filament is preferably formed from wire having a diameter of about 0.005 inches (0.13 mm). The thickness of the balloon 34 is preferably about 0.003 to 0.004 inches (0.08 to 0.1 mm) thick. To prevent the balloon from touching the heater filament the width of the groove should be in the range of 0.002 to 0.04 inches (0.05 to 0.1 mm), and preferably about 0.01 inches (0.25 mm). Similarly, the depth of the groove should be in the range of 0.005 to 0.08 inches (0.13 to 2.0 mm), and preferably about 0.025 inches (0.64 mm). The ratio of width to depth should be in the range of about 1:1 to 1:10, and preferably about 1:2. Otherwise, the width of the groove should be less than twice the thickness of the balloon.

As shown in FIG. 7, the impeller 40 may be enclosed by a cage assembly 115, which prevents the impeller blades 74 from contacting the distensible bladder or balloon 34. Referring additionally to FIG. 8, the impeller cage includes a generally cylindrical or thimble-shaped shell 116, having a plurality of perforations forming fluid ports 118, 119. The proximal end 121 of the cage shell is closed and is configured to be secured to abut the distal end 95 of the heating assembly core 80. The distal end 122 of the impeller cage is generally rounded and closed, but may be formed with additional fluid ports.

The perforations 118 formed proximate the proximal end 121 of the impeller cage shell 116 serve as fluid inlet ports.

The perforations 119 formed proximal the distal end 122 of the cage serve as fluid outlet ports. Various configurations of the cage fluid ports and impeller 40 may provide fluid inlet from the distal ports and fluid outlet from the proximal ports or fluid inlet and outlet from any or all of the ports.

As shown in FIGS. 8 and 8A, the impeller cage assembly 115 further includes an elongate tubular insert 125 which fits into the heating assembly core 80. The proximal end of the insert is disposed proximate the fluid ports 91, 92 configured in the core and the insert distal end is fixed against and secured to the impeller cage shell 116. The insert is configured with a central bore or lumen 103 in which the impeller cable 42 is rotatably disposed. The insert is further configured with one or more longitudinal slots 132 which allow fluid flow from the proximal end 94 of the heating assembly core along the inner surface of the core to the core distal end 95 and into the cage shell.

Referring to FIG. 9, when the impeller blades 74 rotate, pressure gradients formed by the spinning blades draw fluid into the shell 115 of the impeller cage assembly 115 through the proximal inlet ports 118. Similarly, the rotating blades cause fluid to exit the cage through the distal outlet ports 119. As the blades rotate, the blade ends pass over the fluid ports (see also FIG. 6). Thus, a circulation path of fluid, distal to proximal to distal, is developed to minimize temperature gradients within the cavity formed by the inflated balloon 34.

Figure 10:
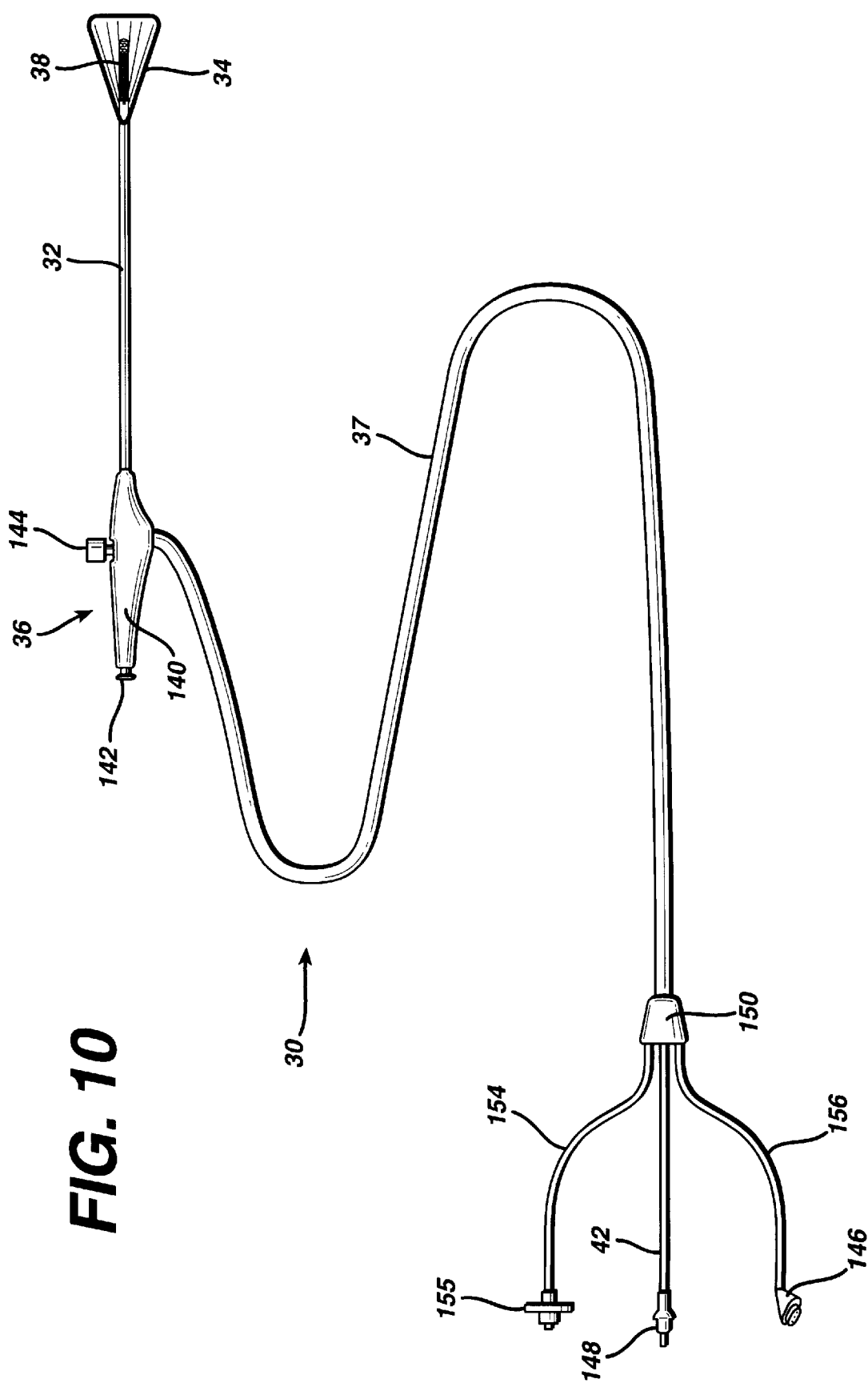
FIG. 10 is a side plan view of the balloon catheter assembly and umbilical cable of the present invention.
Figure 11:
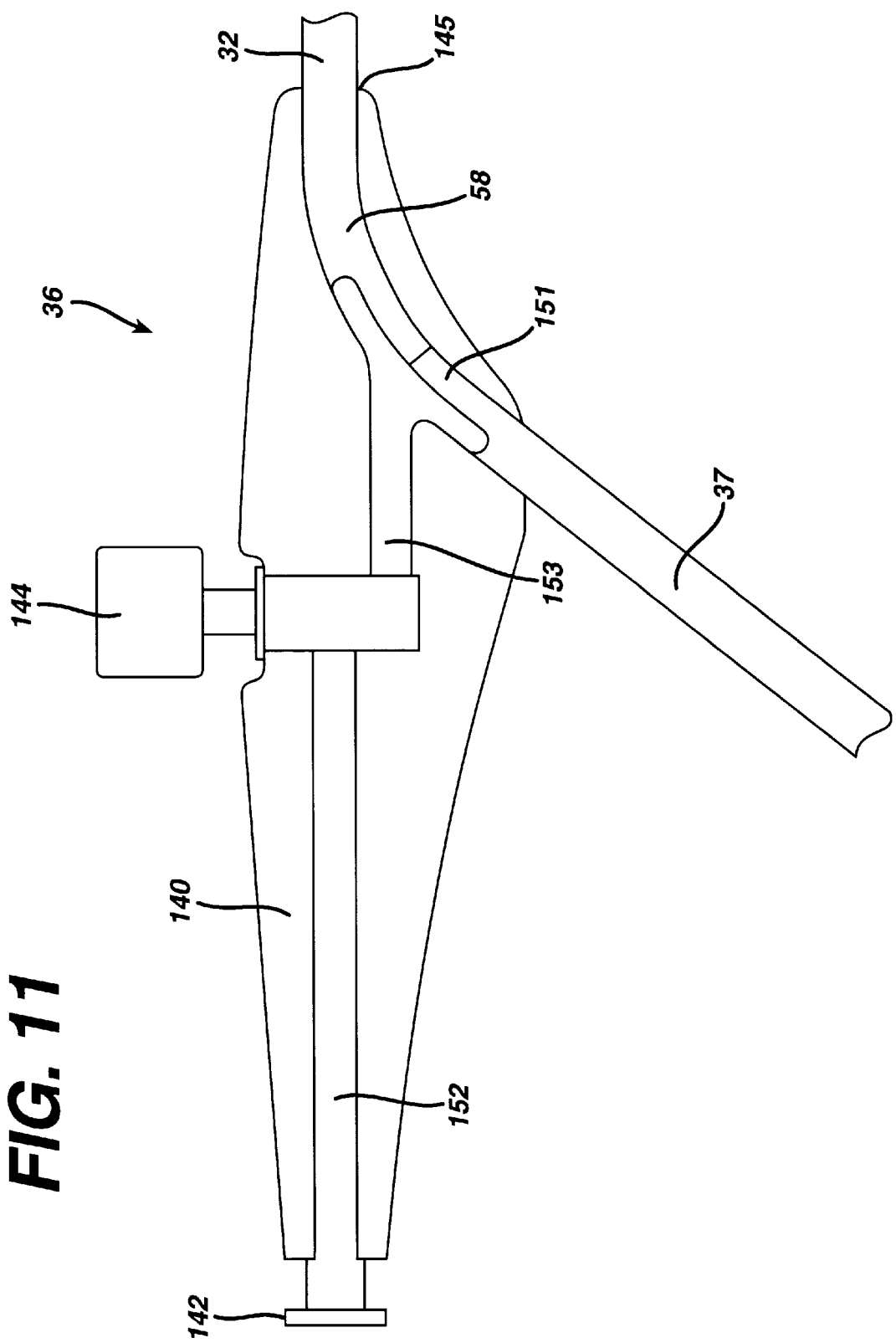
FIG. 11 is a side cross-sectional enlarged view of the proximal handle portion of the balloon catheter assembly of FIG. 10.

As shown in FIG. 10 and in more detail in FIG. 11, the balloon catheter apparatus 30 includes a catheter handle 36 comprising a body 140 configured for providing connection to the catheter tubular member 32. The handle body is configured to retain a fluid fill port 142, to secure a fluid fill valve 144 and to couple with the umbilical cable 37. The handle body is further provided with a slot or similar connector 145 to secure the handle body to the proximal end 58 of the catheter. The handle body is shaped and formed to functionally conform to the human hand.

The fluid fill port 142 of the catheter handle assembly 36 is configured to accept a syringe or other device for introducing an inflation and heating fluid, such as saline, into the catheter fluid lumen 52. The fill port is connected to the fluid fill valve 144 by an inlet conduit 152. An outlet conduit 153 connects the normally-closed fill valve, for example, a trumpet valve, to the catheter fluid lumen and a pressure conduit 154 within the umbilical cable 37.

The proximal end 58 of the catheter tubular member 32 is fixed to or otherwise is disposed proximate the distal end 151 of the umbilical cable 37. Similarly, the connection between the handle outlet conduit 153, the catheter fluid lumen 52 and the pressure conduit 154 may be made by any of several means known to those of ordinary skill. The conduits may be made of suitable plastic tubing, such as vinyl or polyvinyl. The conduits may also be molded or otherwise integrally formed within the handle body.

The fluid fill valve 144 is used to control the fluid pressure supplied to the distensible bladder 34. The outlet conduit 153 is connected to a pressure line or conduit (tap) 154 which is connected to a pressure line port 155, configured outside the handle body 140 and proximal the proximal end 150 of the umbilical cable 37. The pressure port is adapted to accept a connector to the system controller 35 (FIG. 1), which includes a pressure transducer and visual display of the measured pressure in the outlet conduit. The system controller may further provide monitoring and control of the pressure in the fluid passage 52 of the catheter tubular member 32 and balloon 34. Alternatively, a pressure transducer may be disposed within the handle body and connected to the inlet conduit 152, outlet conduit 153 or catheter fluid lumen 52. Such a transducer may be electrically connected to the system controller via electrical leads in the umbilical cable.

When the fluid fill valve 144 is opened, inflation and heating fluid may be supplied to the distensible bladder 34 through a syringe or similar mechanism connected to the fill port 142. The bladder may be inflated to a desired pressure by monitoring a display on the system controller 35 connected to the pressure port 155. Similarly, fluid may be removed from the balloon when the pressure is too high or when desiring complete removal of the balloon catheter apparatus 30 by opening the trumpet valve and withdrawing fluid into the syringe. Creating and maintaining a negative back pressure at the fill port will remove the fluid from the conduits 152, 153 and catheter fluid lumen 52 so as to collapse the distensible bladder against the catheter and heating assembly.

The umbilical cable 37 includes electrical leads for the heating assembly filament 82 and thermocouples 84, 85, which are partially disposed within the catheter tubular member 32 wire lumen 56. The electrical leads extend through the umbilical cable to the umbilical terminator 150 and into a wire bundle 156. The wire bundle is coupled to an electrical connector 146 which couples the heater filament leads to an external power supply in the system controller 35. The electrical connector includes a multiprong connector which is also coupled to each of the plurality (two each) of thermocouple leads. The connecter may be further configured to couple electrical leads from a pressure transducer in the handle body 140 to the system controller. The system controller activates the power to the heating assembly and maintains the temperature in the balloon 34 based on feedback from the thermocouples 84, 85. Visual temperature display and alarms are provided by the controller. Alternatively, an on/off power supply may be provided wherein the heating assembly contains a self-regulating or temperature control device.

The impeller drive cable 42 extends from the distal end of the impeller cage assembly 115 and insert 125, through the heating assembly core 80, through the catheter tubular member 32 and into the handle assembly 36. Within the body 140 of the handle assembly, the impeller cable traverses the proximal end 58 of the catheter tubular member and enters the distal end 151 of the umbilical cable 37. The impeller cable extends through the length of the umbilical cable, through the umbilical terminator 150 and terminates at a rotary connector 148. The rotary connector is configured to couple to the system controller 35, which includes a rotary drive mechanism for turning the impeller cable, and thus the impeller blades 74. The system controller is further configured to start and stop the rotation of the rotary drive mechanism and thus the impeller cable and blades. The system controller monitors the current or similar operation of the drive mechanism and terminates the thermal coagulation procedure or alerts the user if the rotation of the impeller cable or blades is impeded.

The system controller 35 is configured to regulate or control the heat applied to the distensible bladder 34 by controlling the electrical current to the heater filament 82 or other power source for the heating assembly 38. The system controller may include a temperature controller which uses the thermocouples 84, 85 for feedback control to a predetermined or user input set point. The system controller further controls the operating time for which heat is applied to the distensible bladder and monitors the pressure in the distensible bladder and balloon catheter lumen 52. Temperature, pressure and run time displays are also provided. The system controller also initiates and terminates the operation of the rotary drive mechanism which initiates and terminates the rotation of the impeller drive cable 42 and impeller blades 70. Additional features of the system controller are described in U.S. patent application Ser. No. 08/429,960 (WIPO publication number WO 96/33664) and U.S. Pat. No. 4,949,718, the contents of which hereby are incorporated herein by reference.

Referring now to FIGS. 1, 2 and 9, the method of use of the catheter apparatus 30 of the present invention improves circulation of the fluid within the distensible bladder or balloon 34 in view of known ablation systems. During therapy, the uterus 20 may be flattened toward the front and back of the patient or may be similarly asymmetrical. Without the circulation assembly of the present invention, the fluid warmed from contacting the medially located heating assembly 38 moves toward the distal (top) side 160 of the balloon. Similarly, fluid in contact with the proximal (bottom) side 161 of the balloon cools without circulation. Thus, lack of vigorous circulation within the distensible bladder and around the heating assembly may result in different temperatures along the balloon surface 162. Since the surface is different distances from the heating assembly core 80, the surface of the balloon may be unevenly heated by radiation from the heating assembly. The impeller assembly 40, including impeller blades 70, 74 and drive cable 42, of the present invention provide increased circulation of the fluid so as to obtain uniform heating of the balloon surface.

The axially extending blades 70, 74 are rotated to mix the fluid in the distensible bladder 34. One advantage of the impeller blades of the balloon catheter apparatus 30 of the present invention is that the fluid motion is rotary, causing the fluid in the balloon to move in a circular path from the proximal end of the balloon, around the heating assembly 38 and into and around the impeller cage 115 (see arrows FIG. 9). Consequently, the circulation of the fluid reduces or eliminates potential temperature differentials in the balloon.

During operation, the distensible bladder 34 is filled with fluid, rotation of the impeller blades 70 is initiated and heat is applied to the distensible bladder by initiating electric current to the heater filament 82. The rotation of the impeller continues for the duration of the heat therapy. After the power to the heating assembly 38 is turned off and while the fluid in the balloon is cooling, it is advisable to maintain the rotation of the impeller 40 until the fluid reaches the temperature at which the fluid can be safely drained from the balloon. Additional features of the method of use of the apparatus of the present invention are described in U.S. patent application Ser. No. 08/429,960 (WIPO publication number WO 96/33664) and U.S. Pat. No. 4,949,718, the contents of which hereby are incorporated herein by reference.

It will be apparent from the foregoing that, while particular forms of the invention have been illustrated and described, various modifications can be made without departing from the spirit and scope of the invention. Accordingly, it is not intended that the invention be limited, except as by the appended claims.

We claim:

1. An apparatus for thermal coagulation, the apparatus comprising:

an elongate tubular member having a proximal end and a distal end, said tubular member having a first lumen in fluid communication with the proximal end and the distal end;

a handle secured to the proximal end of said elongate tubular member, said handle in fluid communication with the first lumen of said tubular member;

a distensible bladder secured proximate the distal end of said elongate tubular member, said distensible bladder in fluid communication with the first lumen of said tubular member; and a heating element including a tubular core having a surface, a distal end and a proximal end secured to the distal end of said elongate tubular member, the tubular core being disposed within said distensible bladder and configured with a spiral groove forming a plurality of crests and troughs along the surface of the core, said heating element further including a resistive wire wound about the core member and disposed in the spiral groove, such that the resistive wire is prevented from contacting the distensible bladder.

2. The apparatus of claim 1, wherein each trough of the core has a depth and the distance between each crest of the core has a width, such that the ratio of the width to depth is in the range of 1:1 to 1:10.

3. The apparatus of claim 1, wherein each trough of the core has a depth and the distance between each crest of the core has a width, such that the ratio of the width to depth is about 1:2.

4. The apparatus of claim 1, wherein the distensible bladder has a thickness and the distance between each crest of the core has a width, such that the width is less than two times the thickness.

5. The apparatus of claim 1, further comprising a first thermocouple secured proximate the wall of the tubular core of said heating element.

6. The apparatus of claim 5, further comprising a second thermocouple secured proximate the wall of the tubular core of said heating element and positioned about 180 degrees from the first thermocouple.

7. The apparatus of claim 1, further comprising:

an impeller having at least two blades positioned distal of said heating element; and a cable having a distal end secured to said impeller and a proximal end, wherein the cable is partially disposed in said handle, in said tubular member and in the core of said heating element, such that axial rotation of said cable rotates the blades of said impeller.

8. The apparatus of claim 7, further comprising a cage secured to the distal end of the core of said heating element, wherein said impeller is disposed within said cage, such that the impeller blades, when rotated, will not contact said distensible bladder.

9. The apparatus of claim 8, wherein said cage is configured with a plurality of proximal and distal fluid ports, such that when the impeller blades are rotated the fluid within the distensible bladder will enter said cage though the proximal fluid ports and exit said cage through the distal fluid ports.

10. The apparatus of claim 1, wherein said handle further includes:

a body secured to the proximal end of the elongate tubular member;

a fluid fill port in fluid communication with the first lumen of the elongate tubular member and the distensible bladder;

a valve positioned between and in fluid communication with the first lumen of the tubular member and the fluid fill port; and a pressure conduit having a distal end in fluid communication with the first lumen of the tubular member and a proximal end secured to a pressure connector.

11. A method for performing thermal coagulation, the method comprising:
  providing an apparatus as recited in claim 1;
  inflating distensible bladder with a fluid;
  providing electric current to the resistive wire of the heating element;
  heating the inflation fluid within the distensible bladder to a desired temperature; and
  maintaining the temperature of the fluid within the distensible bladder for a desired time interval.

12. An apparatus for thermal coagulation of the endometrium of a uterus, the apparatus comprising:
  (a) a balloon catheter assembly including
    an elongate tubular member having a proximal end and a distal end, the tubular member having a first lumen in fluid communication with the proximal end and the distal end, and
    a distensible bladder secured proximate the distal end of the elongate tubular member, the distensible bladder in fluid communication with the first lumen of the tubular member;
  (b) a heating assembly including
    a tubular core having a surface, a distal end and a proximal end secured to the distal end of the elongate tubular member of the balloon catheter assembly, the tubular core being disposed within the distensible bladder and configured with a spiral groove forming a plurality of crests and troughs along the surface of the core,
    a resistive wire wound about the core member and disposed in the spiral groove, such that the resistive wire is prevented from contacting the distensible bladder,
    at least one thermocouple having a plurality of thermocouple wires, and
    an electrical connector in electrical communication with lead wires partially disposed within a second lumen of the elongate tubular member, the lead wires being in electrical communication with the resistive wire and the plurality of thermocouple wires;
  (c) a circulation assembly including
    an impeller having at least two blades positioned distal of the core of said heating assembly,
    a cage secured to the distal end of the core, wherein the impeller is disposed within the cage such that the impeller blades will not contact said distensible bladder, and
    a cable having a distal end secured to the impeller and a proximal end secured to a rotation connector such that the cable is partially disposed within a lumen of the core and within a third lumen of the tubular member of said balloon catheter assembly, wherein axial rotation of the connector rotates the blades of the impeller;
  (d) a handle assembly including
    a body secured to the proximal end of the elongate tubular member of said balloon catheter assembly,
    a fluid fill port in fluid communication with the first lumen of the elongate tubular member and the distensible bladder,
    a valve positioned between and in fluid communication with the first lumen of the tubular member and the fluid fill port, and
    a pressure conduit having a distal end in fluid communication with the first lumen of the tubular member and a proximal end secured to a pressure connector; and
  (e) an umbilical cable connected to the body of said handle assembly, wherein the lead wires of said heating assembly, the cable of said circulation assembly and the pressure conduit of said handle assembly are partially disposed within said umbilical cable.

13. The apparatus of claim 12, wherein said cage is configured with first fluid ports and second fluid ports, such that when the impeller blades are rotated the fluid within the distensible bladder will enter said cage through the first and second fluid ports and exit said cage through the first and second fluid ports.

14. A method for performing thermal coagulation of the endometrium of the uterus, the method comprising:
  providing an apparatus as recited in claim 12;
  inserting the distensible bladder and a portion of the tubular member into a uterus of a patient;
  opening the valve in the handle;
  introducing a fluid through the fluid fill port into the distensible bladder of the heating assembly;
  inflating the distensible bladder with the fluid;
  closing the valve in the handle assembly;
  providing axial rotation to the cable of the circulation assembly so as to rotate the blades of the impeller;
  providing electrical current to the filament of the heating assembly; and
  heating the fluid within the distensible bladder to a desired temperature for a desired time interval.

15. A system for applying heat to the endometrium of a human uterus, the system comprising:
  (a) a balloon catheter assembly including
    an elongate tubular member having a proximal end and a distal end, the tubular member having a first lumen in fluid communication with the proximal end and the distal end, and
    a distensible bladder secured proximate the distal end of the elongate tubular member, the distensible bladder in fluid communication with the first lumen of the tubular member;
  (b) a heating assembly including
    a tubular core having a surface, a distal end and a proximal end secured to the distal end of the elongate tubular member of the balloon catheter assembly, the tubular core being disposed within the distensible bladder and configured with a spiral groove forming a plurality of crests and troughs along the surface of the core,
    a filament wound about the core member and disposed in the spiral groove such that the filament is prevented from contacting the distensible bladder, wherein heat is generated when an electric current is applied to the filament,
    at least one thermocouple having a plurality of thermocouple wires, and
    an electrical connector in electrical communication with lead wires partially disposed within a second lumen of the elongate tubular member, the lead wires being in electrical communication with the resistive wire and the plurality of thermocouple wires;
  (c) a circulation assembly including
    an impeller having at least two blades positioned distal of the core of said heating assembly,
    a cage secured to the distal end of the core, wherein the impeller is disposed within the cage such that the impeller blades will not contact said distensible bladder, and a cable having a distal end secured to the impeller and a proximal end secured to a rotation connector such that the cable is partially disposed within a lumen of the core and within a third lumen of the tubular member of said balloon catheter assembly, wherein axial rotation of the connector rotates the blades of the impeller;

(d) a handle assembly including
a body secured to the proximal end of the elongate tubular member of said balloon catheter assembly,
a fluid fill port in fluid communication with the first lumen of the elongate tubular member and the distensible bladder,
a valve positioned between and in fluid communication with the first lumen of the tubular member and the fluid fill port, and
a pressure conduit having a distal end in fluid communication with the first lumen of the tubular member and a proximal end secured to a pressure connector; and (e) an umbilical cable connected to the body of said handle assembly, wherein the lead wires of said heating assembly, the cable of said circulation assembly and the pressure conduit of said handle assembly are partially disposed within said umbilical cable; and (f) a controller configured to accept said electrical connector for providing and regulating electrical current to the heating element, wherein the controller is configured to accept the rotational connector for rotating the impeller cable and the controller is further configured to accept the pressure connector for monitoring the pressure of the fluid in the distensible bladder.

16. The system of claim 15, wherein said controller further comprises:
temperature conversion means for generating a temperature signal from the first thermocouple;
temperature display means for visualizing the temperature signal from the temperature conversion means; and
means for electrically connecting the temperature signal to the temperature display means.

17. The system of claim 16, wherein said controller further comprises:
a timer for generating an elapsed time signal;
time display means for visualizing the elapsed time signal; and
means for electrically connecting the elapsed time signal to the temperature display means.

18. The system of claim 17, wherein said controller further comprises a rotation drive mechanism rotatably connectable to the rotation connector of said circulation assembly so as to cause rotation of the blades of the impeller.

19. The system of claim 18, wherein said controller further comprises:
a pressure sensor in fluid communication with the first lumen of said tubular member, the pressure sensor providing a pressure signal;
pressure display means for visualizing the pressure signal; and
means for electrically connecting the pressure signal to the pressure display means.

20. The system of claim 19, wherein said controller further comprising a microprocessor configured to accept the temperature signal, the elapsed time signal and the pressure signal, wherein the microprocessor controls electric current to the filament of the heating assembly and controls the rotation drive mechanism.

21. A method for applying heat to the endometrium of a human uterus, the method comprising:
providing an apparatus as recited in claim 15;
inserting the distensible bladder and a portion of the tubular member of the balloon catheter assembly into a uterus of a patient;
connecting a source of inflation medium to the fluid fill port of the handle assembly;
opening the valve in the handle assembly;
inflating the distensible bladder with the inflation medium to a desired pressure;
closing the valve in the handle assembly;
providing axial rotation to the cable of the circulation assembly so as to rotate the blades of the impeller;
providing electric current to the filament of the heating assembly;
heating the inflation medium within the distensible bladder to a desired temperature as indicated by the thermocouple of the heating assembly;
maintaining the temperature and pressure within the distensible bladder for a desired time interval;
terminating the electric current to the filament of the heating assembly;
allowing the inflation medium within the distensible bladder to cool to a desired temperature;
terminating the axial rotation of the cable so as to stop the blades of the impeller from rotating; and
deflating the distensible bladder by removing the inflation medium; and
removing the distensible bladder and the tubular member of the balloon catheter assembly from the uterus of the patient.

* * * * *